(12) United States Patent
Scivoletto

(10) Patent No.: US 10,507,091 B1
(45) Date of Patent: *Dec. 17, 2019

(54) DENTURE-SECURING DEVICE

(71) Applicant: Joseph C. Scivoletto, Margate, FL (US)

(72) Inventor: Joseph C. Scivoletto, Margate, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/953,890

(22) Filed: Apr. 16, 2018

Related U.S. Application Data

(63) Continuation-in-part of application No. 15/457,452, filed on Mar. 13, 2017.

(51) Int. Cl.
*A61C 13/24* (2006.01)
*A61C 8/00* (2006.01)

(52) U.S. Cl.
CPC ............ *A61C 13/24* (2013.01); *A61C 8/0093* (2013.01)

(58) Field of Classification Search
CPC .................................................. A61C 13/0025
See application file for complete search history.

(56) References Cited

U.S. PATENT DOCUMENTS

| | | | | |
|---|---|---|---|---|
| 1,050,561 A | * | 1/1913 | Moore | A61C 13/0025 433/168.1 |
| 2,392,513 A | * | 1/1946 | Town | A61C 13/0025 433/168.1 |
| 2,628,425 A | * | 2/1953 | Rosner, Jr. | A61C 13/0025 433/168.1 |
| 2,664,631 A | * | 1/1954 | Hollander | A61K 6/083 433/168.1 |
| 3,226,826 A | * | 1/1966 | Town | A61C 13/0025 428/91 |
| 3,845,558 A | * | 11/1974 | Kelly | A61C 13/0025 433/187 |
| 3,886,659 A | * | 6/1975 | Reifke | A61C 13/00 433/188 |
| 4,202,098 A | * | 5/1980 | Russo | A61C 13/0025 433/168.1 |

(Continued)

FOREIGN PATENT DOCUMENTS

| | | |
|---|---|---|
| DE | 1566252 | 11/1970 |
| FR | 2641965 | 7/1990 |

*Primary Examiner* — Ralph A Lewis
(74) *Attorney, Agent, or Firm* — John Rizvi; John Rizvi, P.A.-The Patent Professor ®

(57) ABSTRACT

A denture-securing device is provided that is usable to substantially secure a denture within a mouth. The denture-securing device includes at least one absorbent and flexible pad installable on a first side and an opposite second side of a denture that is affixable to a human gum. The at least one pad comprises an embossed outer side configured to face a human gum when the pad is installed on the denture. The denture-securing device may be used with top dentures, bottom dentures, or other configurations of dentures. The denture-securing device may advantageously secure dentures without requiring use of adhesives. The denture-securing device may also reduce the likelihood of food getting under dentures, provide a firm yet soft and comfortable fit, and minimize rocking of lower dentures. The denture-securing device may advantageously be secured to gums using a suction fit through saliva or other sources of moisture.

17 Claims, 15 Drawing Sheets

(56) References Cited

U.S. PATENT DOCUMENTS

| | | | |
|---|---|---|---|
| 4,867,681 A * | 9/1989 | Knospins | A61C 13/0025 |
| | | | 433/180 |
| 5,431,563 A | 7/1995 | Huybrechts | |
| 7,195,484 B1 | 3/2007 | Wagner | |
| 2007/0134622 A1 * | 6/2007 | Rajaiah | A61C 19/063 |
| | | | 433/168.1 |
| 2010/0248183 A1 | 9/2010 | Tudek et al. | |
| 2013/0191518 A1 | 7/2013 | Narayanan et al. | |
| 2015/0235282 A1 | 8/2015 | Kamath | |
| 2017/0277909 A1 | 9/2017 | Kraemer et al. | |
| 2018/0211043 A1 | 7/2018 | Husain | |

* cited by examiner

DENTURE-SECURING DEVICE

CROSS-REFERENCE TO RELATED APPLICATIONS

This application is a Continuation-In-Part of U.S. Utility patent application Ser. No. 15/457,452, filed on Mar. 13, 2017, which is incorporated by reference herein in its entirety.

FIELD OF THE INVENTION

The invention relates to a denture-securing device. More particularly, the invention relates to a denture pad useful for securing dentures to human gums without the use of adhesives.

BACKGROUND OF THE INVENTION

Dentures are replacements for missing teeth and normally consist of a curved plate carrying one or more artificial teeth and configured to fit onto the upper or lower gums. Typically, a denture user can wear a denture during normal, everyday life and optionally remove the denture when desired, such as for sleeping or for washing and maintaining the denture.

The irregularities of the contours of the upper and lower gums traditionally pose difficulties with fixing dentures in a position within a mouth. These difficulties are heightened as the contours of the gums may continually change as the mouth moves during normal use. Various solutions have been proposed to overcome these difficulties, but such solutions fail to provide a substantially secure attachment of dentures within the mouth as the denture may move during normal use. Examples of such incomplete solutions include use of powdered adhesives, viscous materials, and other undesirable adhesive products. As an additional disadvantage of using adhesive products, saliva may reduce the viscosity or adhesive properties of such products. Furthermore, saliva containing adhesives may be accidentally swallowed leading to stomach irritation.

Therefore, there remains a need for a solution to at least one of the aforementioned problems. For instance, a denture-securing device is needed that may substantially secure dentures to gums, preferably without requiring adhesives. Preferably, a cleanable and reusable denture-securing device is desired. It is also desirable that the denture-securing device can be constructed using materials having a low likelihood of irritating the inside of the mouth or stomach and no association with causing serious health problems.

SUMMARY OF THE INVENTION

A denture-securing device is described herein that substantially secure a denture to a user's gum within a user's mouth without requiring adhesives. The denture-securing device is also secured to a denture. The denture-securing device is cleanable and reusable and can be constructed using materials having a low likelihood of irritating the inside of the mouth or stomach and causing any health problems. These materials may be folded a number of times, for example, 8 to 12 times, to increase absorption properties of water or saliva by the denture-securing device. The denture-securing device may be substantially zinc free.

The denture-securing device may be provided in multiple pieces, which may be applied to one or more dentures. For example, the denture-securing device may include a first pad and a second pad that can be placed on surfaces of the dentures that will interface with the gums to which the dentures will be installed. This use of multiple pads may be applicable to both upper and lower dentures. The pads may be trimmed to fit dentures of various sizes and shapes. In another embodiment, the denture-securing device may be constructed as a single unitary piece.

In a first implementation of the invention, a denture-securing device for securing a denture to a human gum comprises at least one absorbent and flexible pad installable on a first side and an opposite second side of a denture that is affixable to a human gum. The at least one pad comprises an embossed outer side configured to face a human gum when the pad is installed on the denture. The at least one pad is configured to adopt a working position in which the at least one pad is flexed, installed on the denture and sandwiched between the denture and a human gum, and further in which the at least one pad is moistened and adhered to the human gum via suction of the human gum towards the embossed outer side of the at least one pad.

In a second aspect, the at least one pad can be arranged folded over an outer edge of the denture, and overlapping and in contact with an outer face of the denture when the at least one pad is in the working position.

In another aspect, the at least one pad can include a first pad installable on the first side of the denture and a separate, second pad installable on the opposite second side of the denture. Alternatively, the at least one pad can include a single pad installable on the first side, the opposite second side and a front side of the denture extending from the first side to the second side of the denture.

In another aspect, the at least one pad can be comprised of multiple layers of material. For example, the multiple layers of material can include an outer layer providing the embossed outer side, an inner layer providing an inner surface configured to contact the denture, and an intermediate layer sandwiched between the outer layer and the inner layer. The outer layer can be made of pure cellulose. The inner layer can be made of spun lace cotton. The intermediate layer can be made of cotton.

In another aspect, the multiple layers of material can include at least two separate pieces of the material arranged in layers. Alternatively, the multiple layers of material comprise a single piece of material folded so as to be configured into at least two layers. In other embodiments, the multiple layers of material can include at least two separate pieces of material, wherein each separate piece of material is folded so as to be configured into at least two layers, and wherein the at least two separate pieces of material are arranged in layers after folding.

In another aspect, the pad can be constructed from wood pulp paper.

In another aspect, the pad can be constructed from fabric, cotton, pure cellulose, linen fibers, lignin, spun lace cotton, or a combination thereof.

In another aspect, the pad can be cleanable and reusable.

In another aspect, the at least one pad can be placed into a channel of the first side and the second side of the denture when in the working position.

In another aspect, the denture can be an upper denture or a lower denture.

In another aspect, the at least one pad can be moistened by saliva or water present in a user's mouth.

In another aspect, supplements may be added to the denture-securing device to provide minerals or other contents to a user. For example, mastic drops may be administered or otherwise included by the denture-securing device for delivery to a user, such as via the gums.

A method of the invention can be used for affixing a denture to a gum. The method includes the steps of: (a) placing at least one pad having multiple layers of material for placement on a denture; and (b) affixing the denture to a human gum by moistening the at least one pad.

Another method of the invention can include the step of installing the at least one pad into a channel of the denture.

Another method of the invention can include the step of moistening the at least one pad with saliva, water, or another suitable solution.

Another method of the invention can include the step of folding an edge of the at least one pad at least partially over a front of the denture to secure the at least one pad to the denture.

Another method of the invention can include the at least one pad including a first pad installable on a first side of the denture and a second pad installable on a second side of the denture. The first pad can include a first pad miter edge and the second pad can include a second pad miter edge. The first and second pads adjoin at their respective miter edges. A front portion of the first pad miter edge and a front portion of the second pad miter edge fold at least partially over a front of the denture. The method further includes the step of: folding the first pad miter edge and the second pad miter edge of the at least one pad at least partially over a front of the denture to secure the at least one pad to the denture.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents and other references mentioned herein are incorporated by reference in their entirety. In the case of conflict, the present specification, including definitions will control.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

Figure 1:
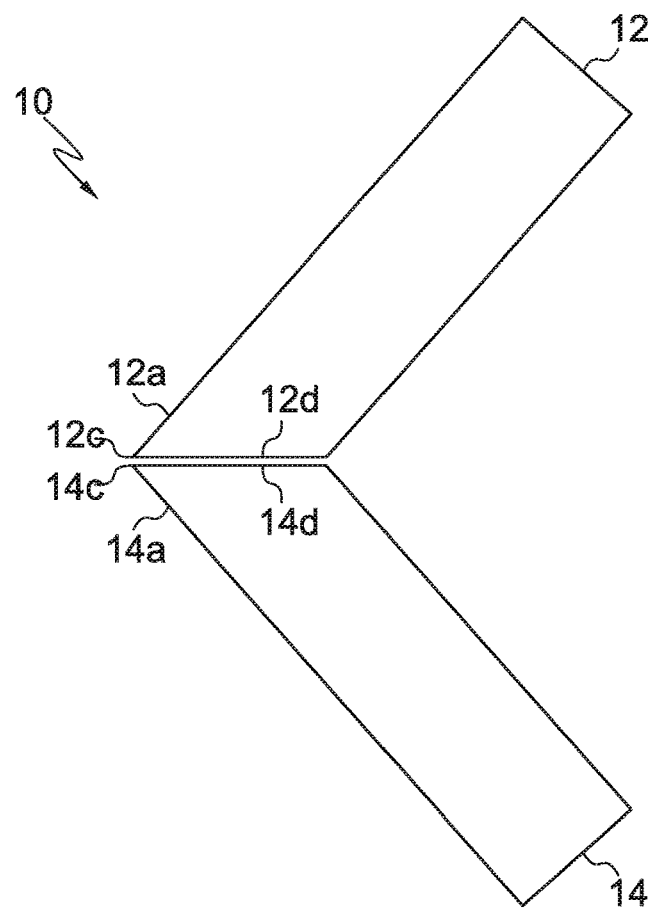
FIG. 1 is a top plan view of the denture-securing device according to an embodiment of the present invention wherein the denture-securing device includes a first pad and a second pad.

The present invention is best understood by reference to the detailed drawings and description set forth herein. Embodiments of the invention are discussed below with reference to the drawings; however, those skilled in the art will readily appreciate that the detailed description given herein with respect to these figures is for explanatory purposes as the invention extends beyond these limited embodiments. For example, in light of the teachings of the present invention, those skilled in the art will recognize a multiplicity of alternate and suitable approaches, depending upon the needs of the particular application, to implement the functionality of any given detail described herein beyond the particular implementation choices in the following embodiments described and shown. That is, numerous modifications and variations of the invention may exist that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

The present invention should not be limited to the particular methodology, compounds, materials, manufacturing techniques, uses, and applications, described herein, as these may vary. The terminology used herein is used for the purpose of describing particular embodiments only, and is not intended to limit the scope of the present invention. As used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" may be a reference to one or more steps or means and may include sub-steps and subservient means.

All conjunctions used herein are to be understood in the most inclusive sense possible. Thus, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should be read as "and/or" unless expressly stated otherwise. Structures described herein are to be understood also to refer to functional equivalents of such structures. Language that may be construed to express approximation should be so understood unless the context clearly dictates otherwise.

Unless otherwise defined, all terms (including technical and scientific terms) are to be given their ordinary and customary meaning to a person of ordinary skill in the art, and are not to be limited to a special or customized meaning unless expressly so defined herein.

Terms and phrases used in this application, and variations thereof, especially in the appended claims, unless otherwise expressly stated, should be construed as open ended as opposed to limiting. As examples of the foregoing, the term "including" should be read to mean "including, without limitation," "including but not limited to," or the like; the term "having" should be interpreted as "having at least"; the term "includes" should be interpreted as "includes but is not limited to"; the term "example" is used to provide exemplary instances of the item in discussion, not an exhaustive or limiting list thereof; and use of terms like "preferably," "preferred," "desired," "desirable," or "exemplary" and words of similar meaning should not be understood as implying that certain features are critical, essential, or even important to the structure or function of the invention, but instead as merely intended to highlight alternative or additional features that may or may not be utilized in a particular embodiment of the invention.

Those skilled in the art will also understand that if a specific number of an introduced claim recitation is intended, such an intent will be explicitly recited in the claim, and in the absence of such recitation no such intent is present. For example, as an aid to understanding, the appended claims may contain usage of the introductory phrases "at least one" and "one or more" to introduce claim recitations; however, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C" is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The invention provides a denture-securing device usable to substantially secure dentures within a mouth. The denture-securing device may be used with top dentures, bottom dentures, or other configurations of dentures. The denture-securing device may advantageously secure dentures without requiring use of adhesives. The denture-securing device may also reduce the likelihood of food getting under dentures, provide a firm yet soft fit, and minimize rocking of lower dentures and partials. The denture-securing device may advantageously be secured to gums using a suction fit. The number of denture-securing devices required by a user is determined by the number of dentures the user wears in his or her mouth. For example, for a person having only an upper denture or only a lower denture, only one denture-securing device is needed. However, for a user who wears both upper and lower dentures, one denture-securing device is used to secure the upper denture to an upper gum in the user's mouth and a second denture-securing device is used to secure the lower denture to a lower gum in the user's mouth.

Figure 2:
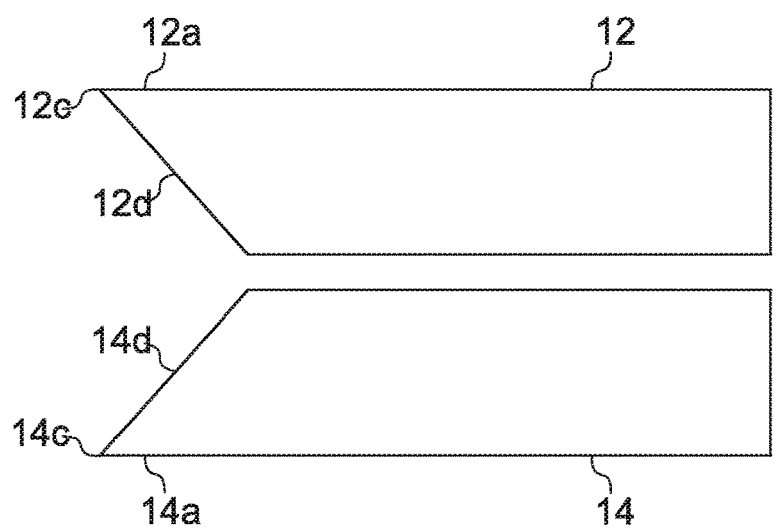
FIG. 2 is another top plan view of the first pad and second pad of the denture-securing device of FIG. 1.
Figure 3:
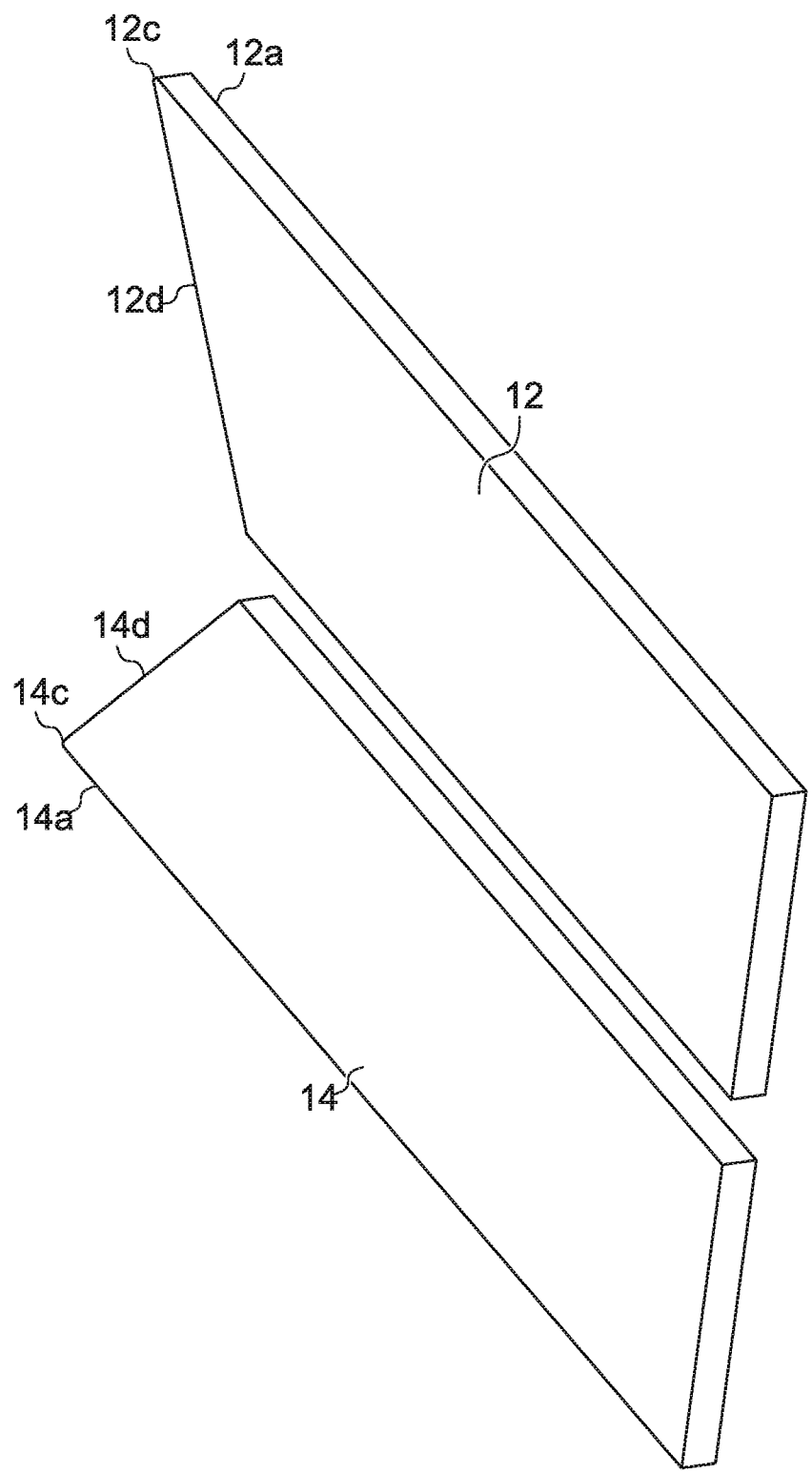
FIG. 3 is a perspective view of the first pad and second pad of the denture-securing device of FIG. 1.

Referring now to FIGS. 1-2, a denture-securing device 10 in accordance with the present disclosure will be discussed in more detail. The denture-securing device 10 may function as a pad and also serves to reline and bond a denture. The denture-securing device 10 may be constructed using a folded piece of material that is formed into a pad 10. For example, the pad may be constructed using a folded paper product. In one embodiment, the folded paper product may be 100% wood pulp paper material. The material may be folded a number of times to achieve the desired thickness and other properties. In one example, the material may be folded between about 8-12 times. Skilled artisans will appreciate the material may also be folded, stacked, and/or placed one on top of the other, 1, 2, 3, 4, 5, 6, 7, 8, 9, 10, 11, 12, 13, 14, 15, 16, 17, 18, 19, 20, or more times, without limitation. In one embodiment, a single piece of material can be folded one or more times to create the pad or denture-securing device 10. In another embodiment, two or more pieces of material may each be folded one or more times and layered one upon another to form the pad. In still another embodiment, one or more unfolded pieces of material and one or more pieces of material that have been folded one or more times may be layered one upon another to form the pad. In yet another embodiment, two or more unfolded pieces of material are layered one upon another to form the pad. In another embodiment, a single unfolded piece of material forms the pad. In at least one embodiment, the denture-securing device is constructed without using cotton.

Folding the denture-securing device may be advantageous over using a puffy napkin configuration, as the folded denture-securing device provides for better water absorption, smaller and flatter form, improved fit around the gums, and reduced undesired expansion caused by absorption typical to traditional puffy napkins. The material may be a fabric material, such as a paper fabric material. In an alternative embodiment, the material may include polyester as a spun lace or non-spun lace. The material of the denture-securing device may be absorbent of water, saliva, and other liquids. Preferably, the material used to construct the denture-securing device is substantially zinc-free.

The denture-securing device may be cleanable. More particularly, the denture-securing device may be separable from the dentures and cleanable between applications for reuse. In one example, the denture-securing device may be separated from a denture when a user removes his or her dentures before going to sleep. In another example, the denture-securing device may be separated from the dentures after a user eats. The denture-securing device may be cleaned using water, denture cleaning tablets, and other cleaning products that would be appreciated by a skilled artisan. The denture-securing device may be at least partially submerged in water or another cleaning product as the denture-securing device is cleaned. For example, the denture-securing device may be cleaned in a denture back along with the dentures to which it may be installed, allowing for saturation during cleaning. Once the denture-securing device has been cleaned, it may be removably installed in the denture and reused.

Saliva in the user's mouth moistens the denture-securing device so that when it is installed in a channel of a denture and secured to a gum of the user in the user's mouth, the saliva creates a suction between the denture-securing device and the user's gum.

A liquid may be applied to the denture-securing device prior to installation and/or locating the dentures in the mouth. This liquid may advantageously reduce an undesirable dry mouth condition that may otherwise be experienced by some users. The liquid may include water, saliva, saline, or other liquids that would be appreciated by a skilled artisan. Additionally, supplemental ingredients may be added to the denture-securing device to add or alter the device. For example, mastic drops may be added to the denture-securing device so that a user may receive minerals upon placing dentures with the denture-securing device in his or her mouth. The mastic drops may be derived from mastic gum, such as an herb mastic gum. An antibacterial composition may optionally be included by the denture-securing device.

In another example, moisture may be added to the denture-securing device to improve hydration in the mouth of the user. The denture-securing device may be pre-soaked in its packaging, which may at least partially moisten the pad with water or another fluid to advantageously reduce reliance on saliva of the user to create suction to install the denture to the gums. A presoaked embodiment of the denture-securing device may be especially desirable to remedy dry mouth conditions that may otherwise be present in some users.

The denture-securing device may be constructed using a fibrous paper material, which may share similar properties with a moist towelette. The surface of the denture-securing device may be generally smooth. The denture-securing device may create its own suction, eliminating the need of suction pads or recesses.

In one embodiment of this disclosure, the denture-securing device may be configured as a single pad shaped to fit within a denture. In another embodiment of this disclosure, the denture-securing device may be configured as multiple pads, for example a first pad and a second pad. The first pad and second pad may have the same or similar dimensions. However, skilled artisans will appreciate that the first pad, second pad, and any other pads may have dimensions that differ from one another.

Figure 4:
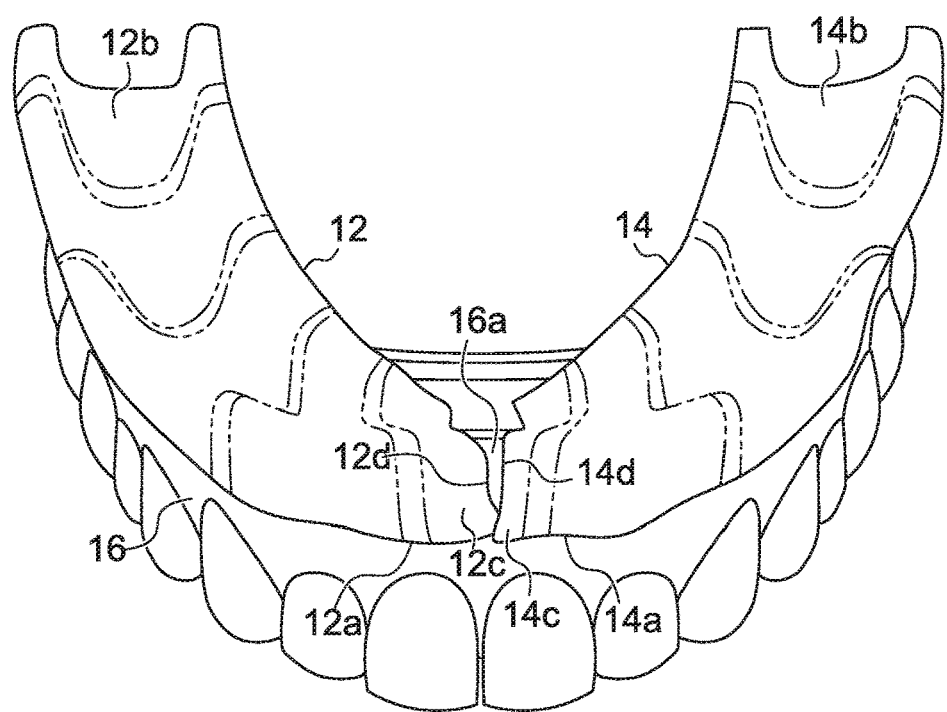
FIG. 4 is a front perspective view of the first pad and second pad of the denture-securing device of FIG. 1 installed on an upper denture.
Figure 5:
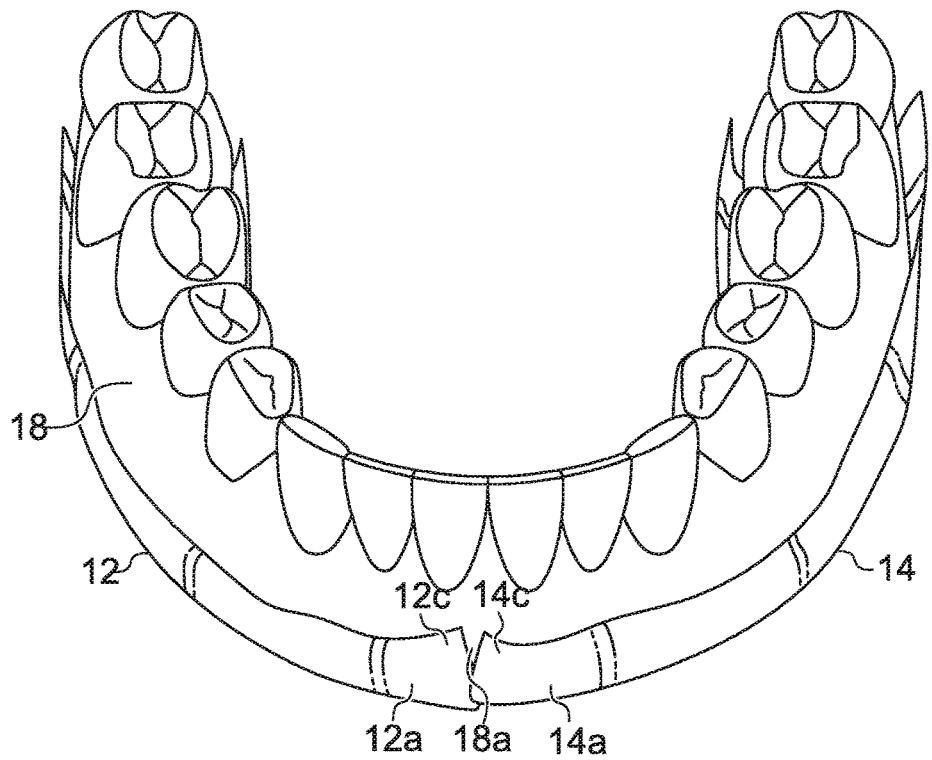
FIG. 5 is a front perspective view of the first pad and second pad of the denture-securing device of FIG. 1 installed on a lower denture.
Figure 6:
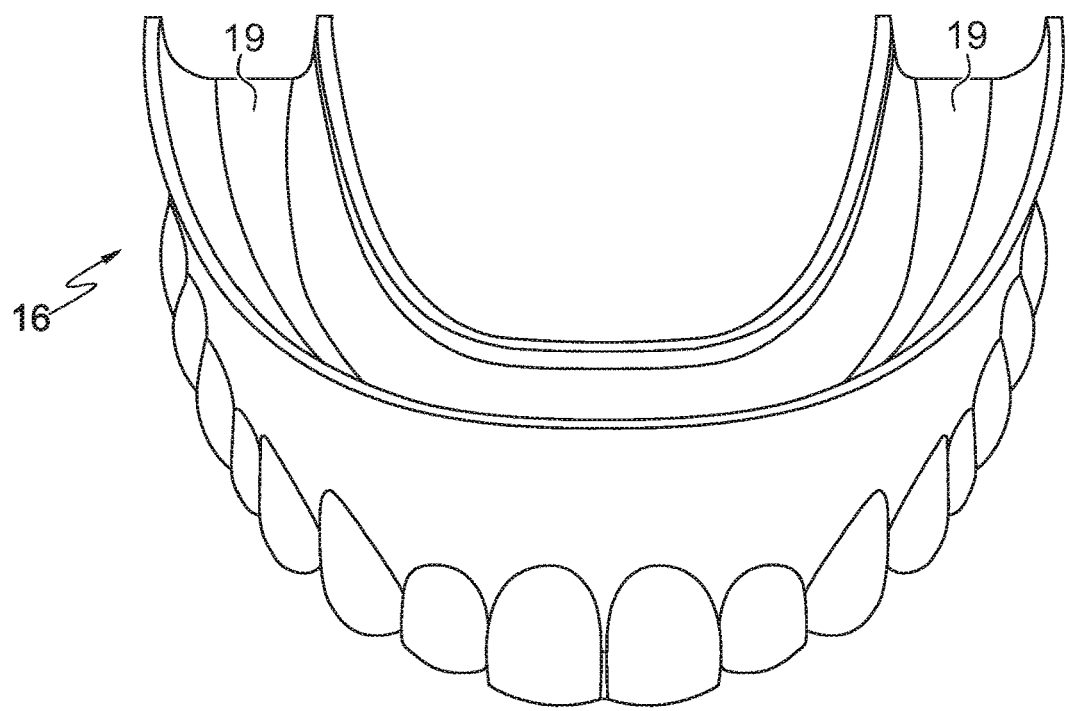
FIG. 6 is a front perspective view of the upper denture of FIG. 4 without the first pad and second pad of the denture-securing device installed thereon.
Figure 7:
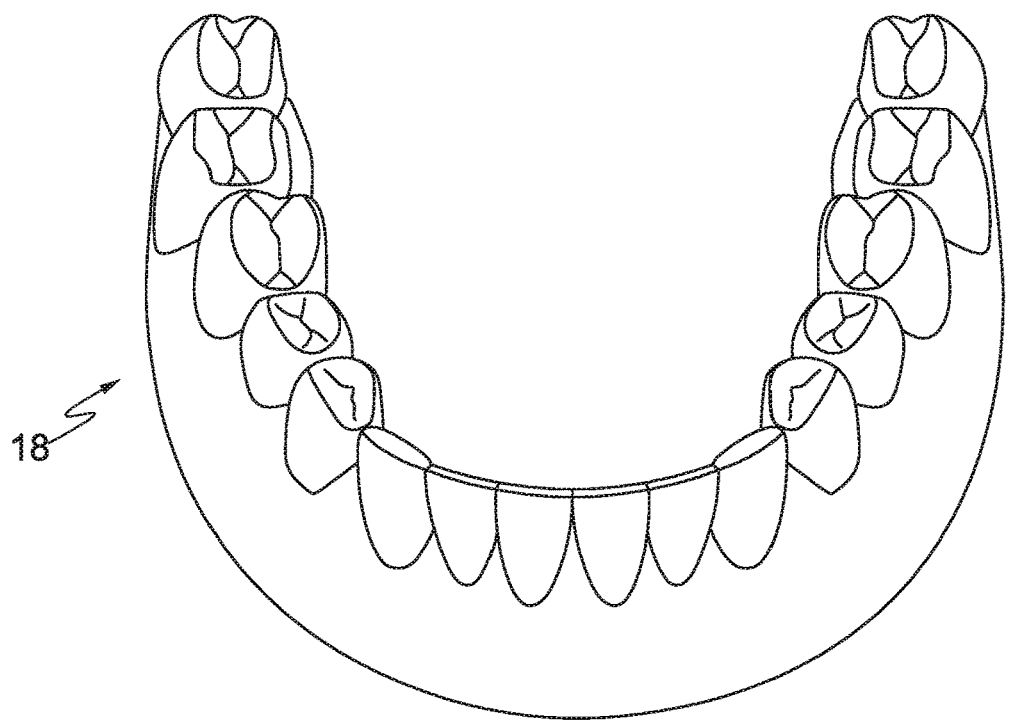
FIG. 7 is a front perspective view of the lower denture of FIG. 5 without the first pad and second pad of the denture-securing device installed thereon.

Referring to FIGS. 1-5, an illustrative embodiment including two pads will be discussed. The illustration of FIG. 1 shows a first pad 12 and a second pad 14 of the denture-securing device 10 in a substantially flat configuration. As shown in FIGS. 1 and 2, a first end 12a of the first pad 12 may be positioned near a first end 14a of the second pad 14. As illustrated in FIG. 4, the first pad 12 and the second pad 14 of the denture-securing device 10 may be placed onto the gum-facing side of an upper denture 16. The illustration of FIG. 5 shows the first pad 12 and the second pad 14 of a second denture-securing device 10 placed onto the gum-facing side of a lower denture 18. The first ends 12a, 14a of the first pad 12 and the second pad 14 may be placed so that the first ends 12a, 14a do not touch or partially overlap. The first pad 12 of the denture-securing device 10 may at least partially conform to the gum-facing surface of the denture 16 or 18 to which it is installed, creating a first pad channel 12b along the center of the denture channel 19 (shown in FIG. 6) longitudinally to interface with the gum. Similarly, the second pad 14 of the denture-securing device 10 may at least partially conform to the gum-facing surface of the dentures, creating a second pad channel 14b along the center of the denture channel 19 longitudinally to interface with the gum. The illustrations of FIGS. 6 and 7 show the upper and lower dentures 16 and 18, respectively; while the denture channel 19 of the upper denture 16 is shown in FIG. 6, the denture channel of the lower denture 18 is not visible in FIG. 7 but is otherwise similar to the denture channel 19 of the upper denture 16.

With reference to FIGS. 1 and 2, one or both of the first pad 12 and the second pad 14 can include a foldable front portion 12c, 14c, which is foldable over a front portion 16a, 18a of the denture 16 or 18 to which each pad is installed. The foldable front portion 12c of the first pad 12 and the foldable front portion 14c of the second pad each have a miter edge so that when installed to a denture, their arrangement (if not partially overlapping) is similar to a miter joint as shown in FIGS. 1 and 4. The foldable front portions 12c, 14c of the first pad 12 and second pad 14 securely affix the denture-securing device 10 to the denture. By folding the foldable front portions over the front portion of the denture, the denture-securing device achieves a more secure attachment to the denture, without the use of adhesives, than conventional denture pads that are installed only within the denture channel of a denture and that do not include any portion that folds over the front portion of the denture.

Figure 8:
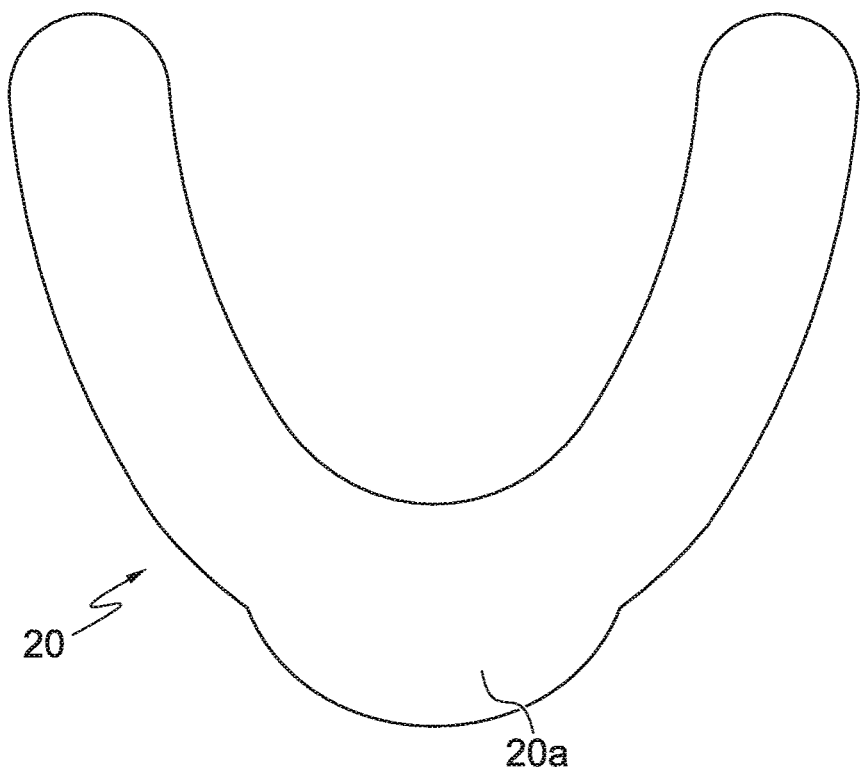
FIG. 8 is a top perspective view of a denture-securing device according to an embodiment of the present invention wherein the denture-securing device is constructed as a single unitary pad and is shaped to correspond to the denture channel of a denture.
Figure 9:
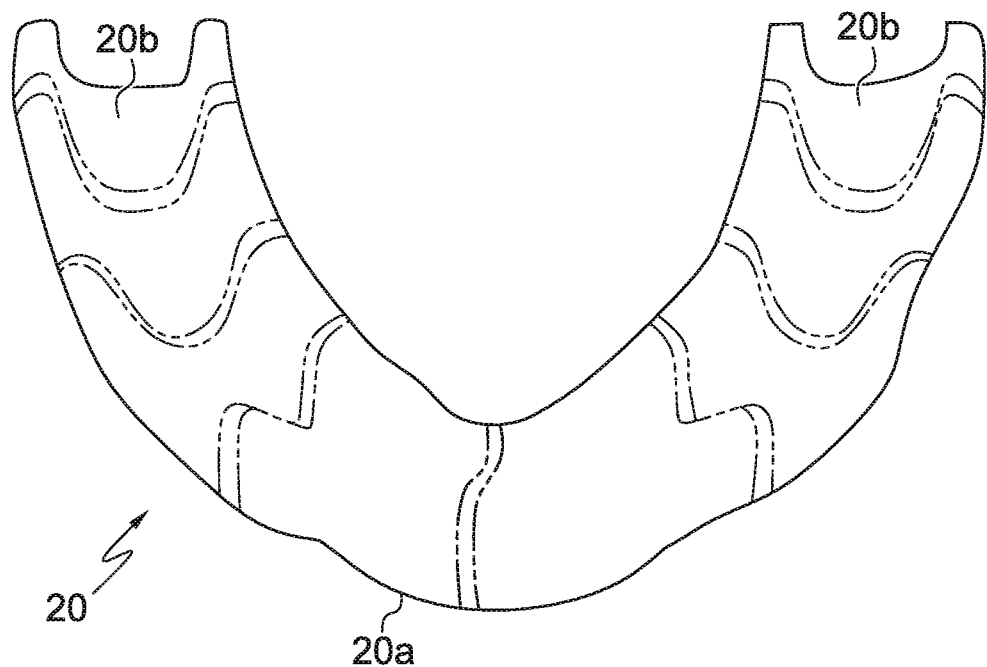
FIG. 9 is a top perspective view of the denture-securing device of FIG. 6, wherein a front portion of the single unitary pad is folded forward for securement to an upper gum when installed in a denture channel of an upper denture.
Figure 10:
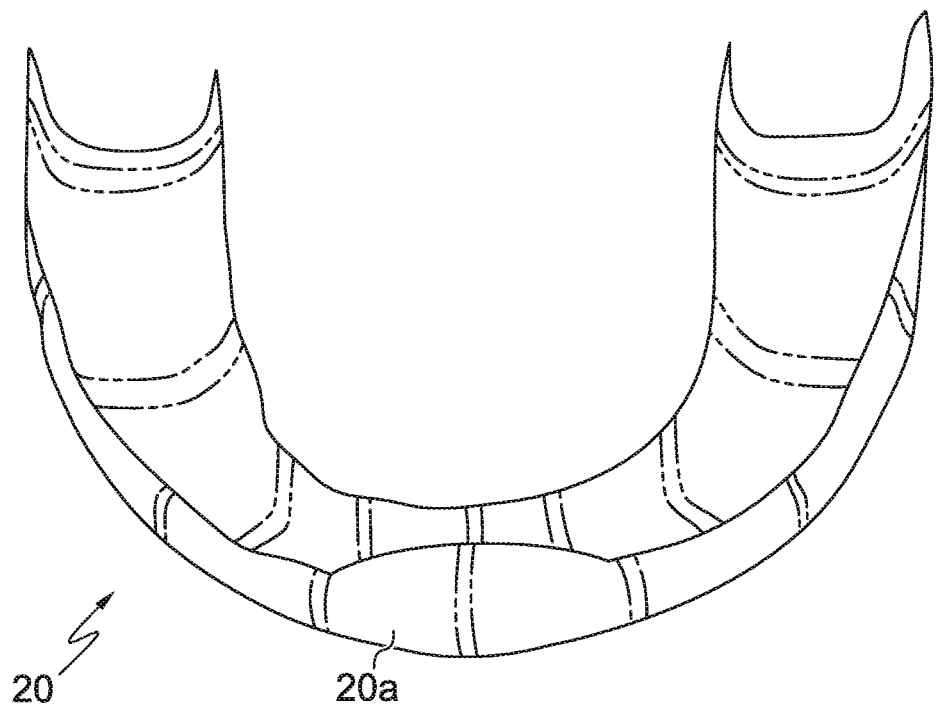
FIG. 10 is a top plan view of the denture-securing device of FIG. 6 before the single unitary pad is installed in a denture channel.
Figure 11:
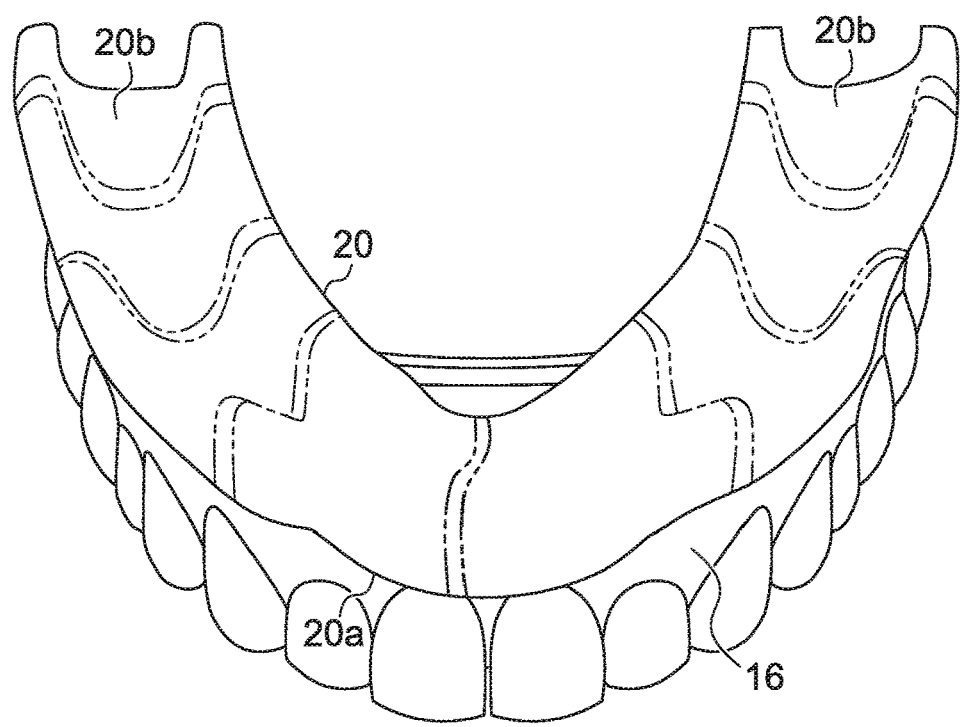
FIG. 11 presents a front view of the denture-securing device of FIG. 9, shown installed on a top denture.
Figure 12:
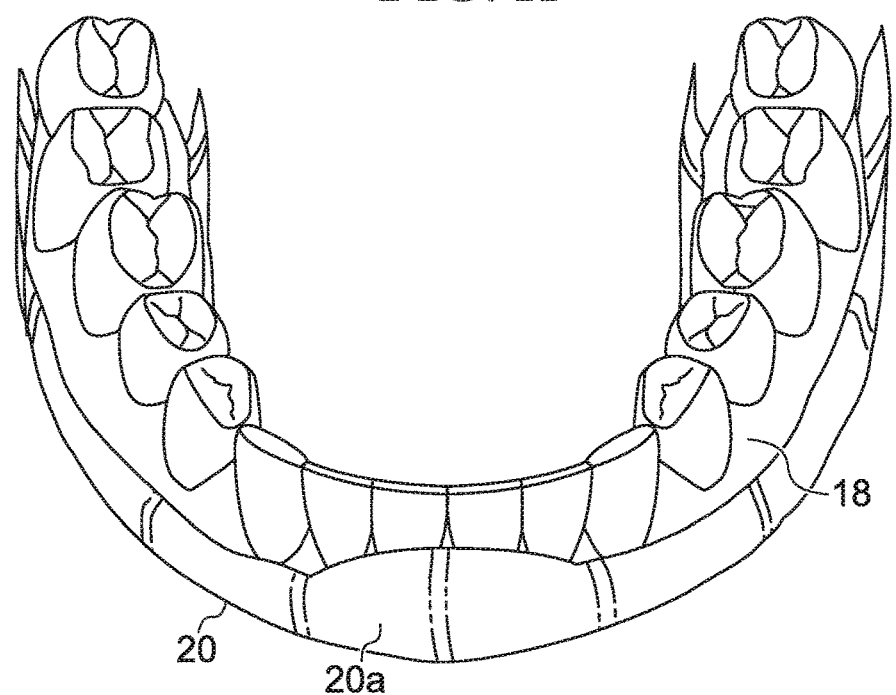
FIG. 12 presents a front view of the denture-securing device of FIG. 10, shown installed on a bottom denture.

The illustrations of FIGS. 8-10 show a second illustrative embodiment of the denture-securing device 20 that is constructed as a single unitary pad rather than as two or more pads. In FIGS. 9 and 10, the single unitary pad, denture-securing device 20 is shown formed into the shape the pad or denture-securing device 20 takes when installed in a denture channel, e.g., while installed in the denture channel or after removal from a denture channel. The single unitary pad, denture-securing device 20 forms a pad channel 20b when installed in (and after removal from) a denture channel. In FIG. 9, the single unitary pad 20 is shown with a front edge 20a folded downward as it would be when installed on a lower denture to secure the pad to the gum. In FIG. 10, the single unitary pad 20 is shown with a front edge 20a folded upward as it would be when installed on an upper denture to secure the pad to the gum.

As the dentures with the denture-securing device installed, which may include one or multiple pads, are compressed against the gums, the denture-securing device may create suction due to the presence of saliva or other moisture to substantially secure the dentures against the gums. The suction created may be sufficient to hold the dentures to the gums, but not so strong as to cause discomfort to the user.

Figure 14:
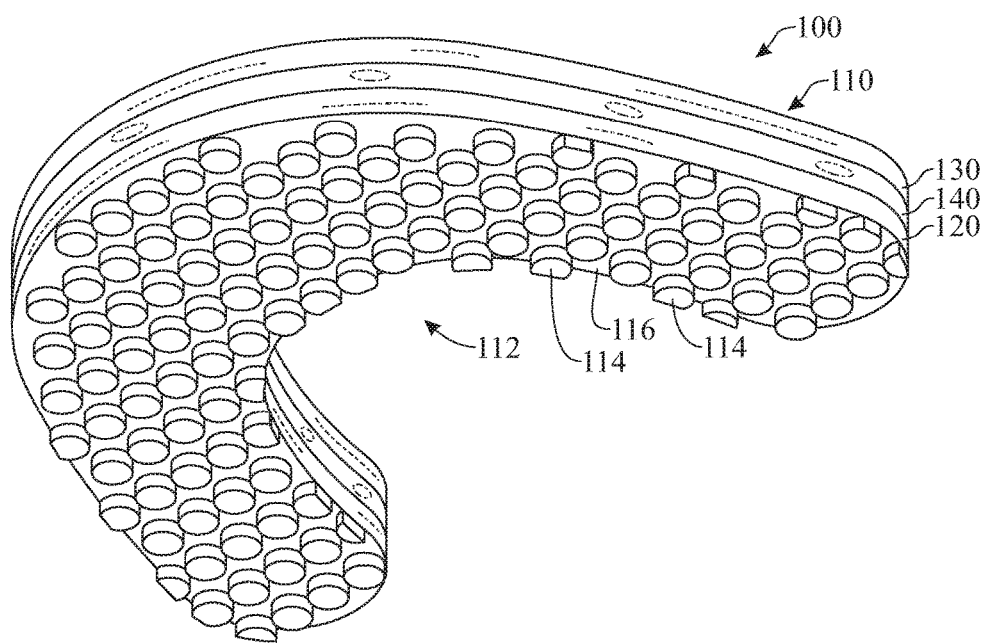
FIG. 14 presents a bottom perspective view of the denture-securing device of FIG. 13.
Figure 15:
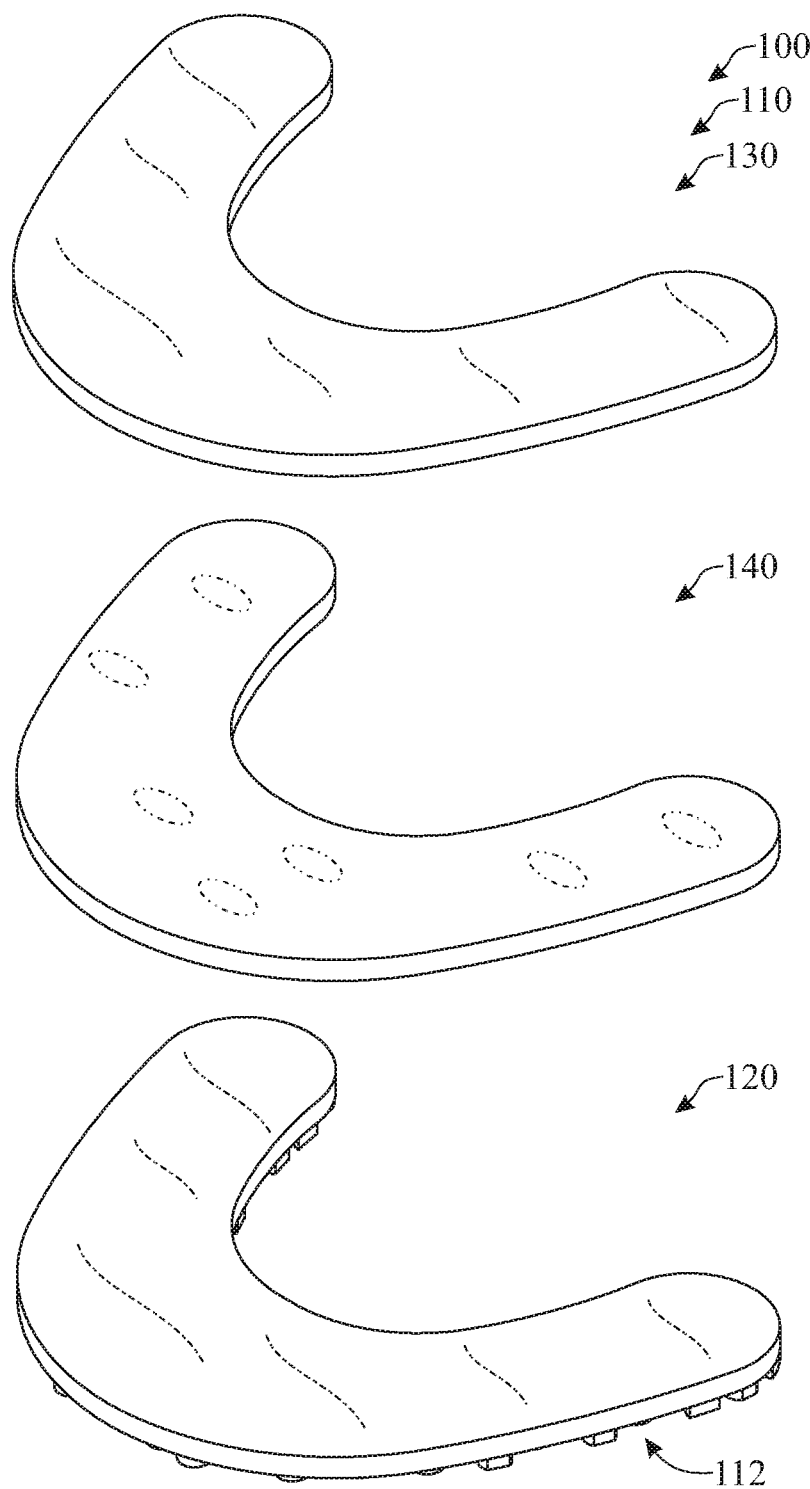
FIG. 15 presents an exploded, top perspective view of the denture-securing device of FIG. 13, illustrating three layers forming the pad.
Figure 16:
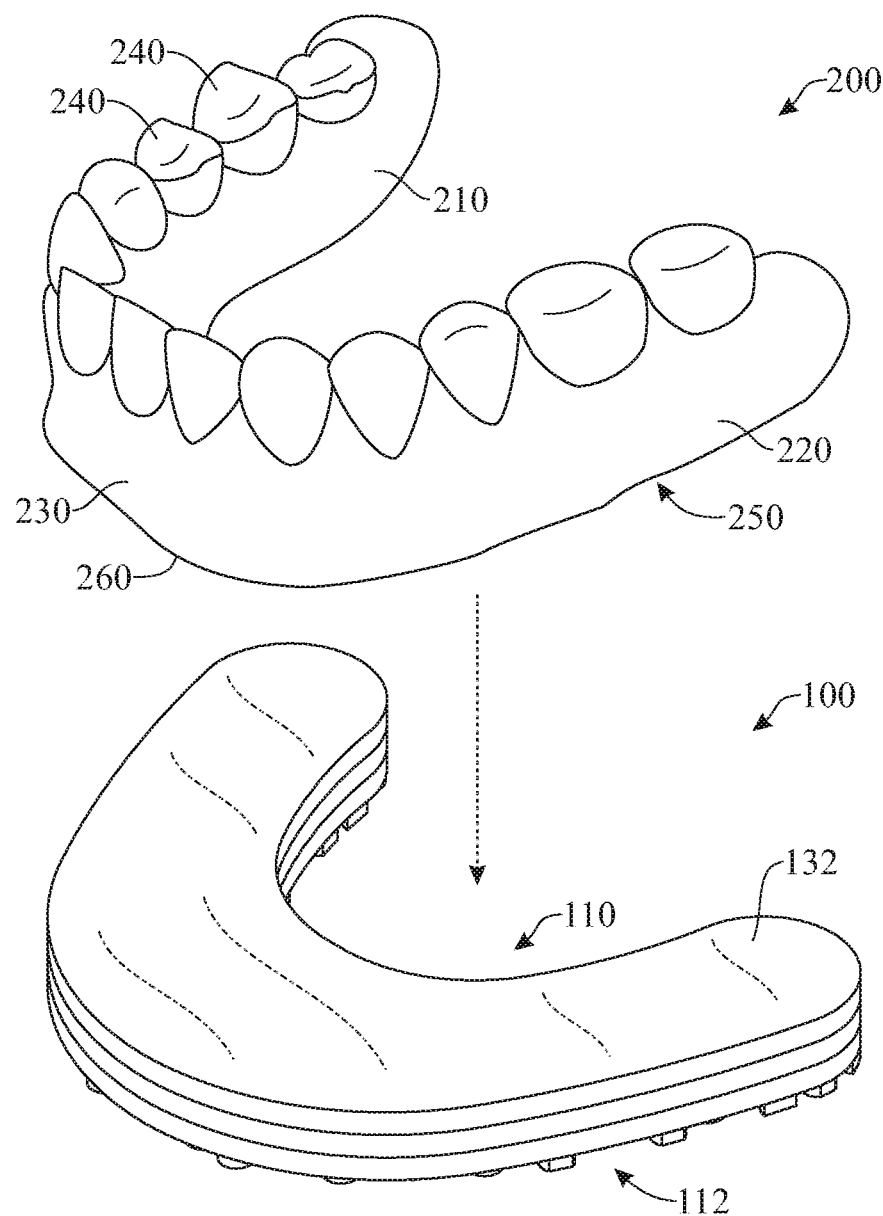
FIG. 16 presents a perspective view illustrating a first step of installing the denture-securing device, and more specifically a step of attaching the denture-securing device to a denture.
Figure 20:
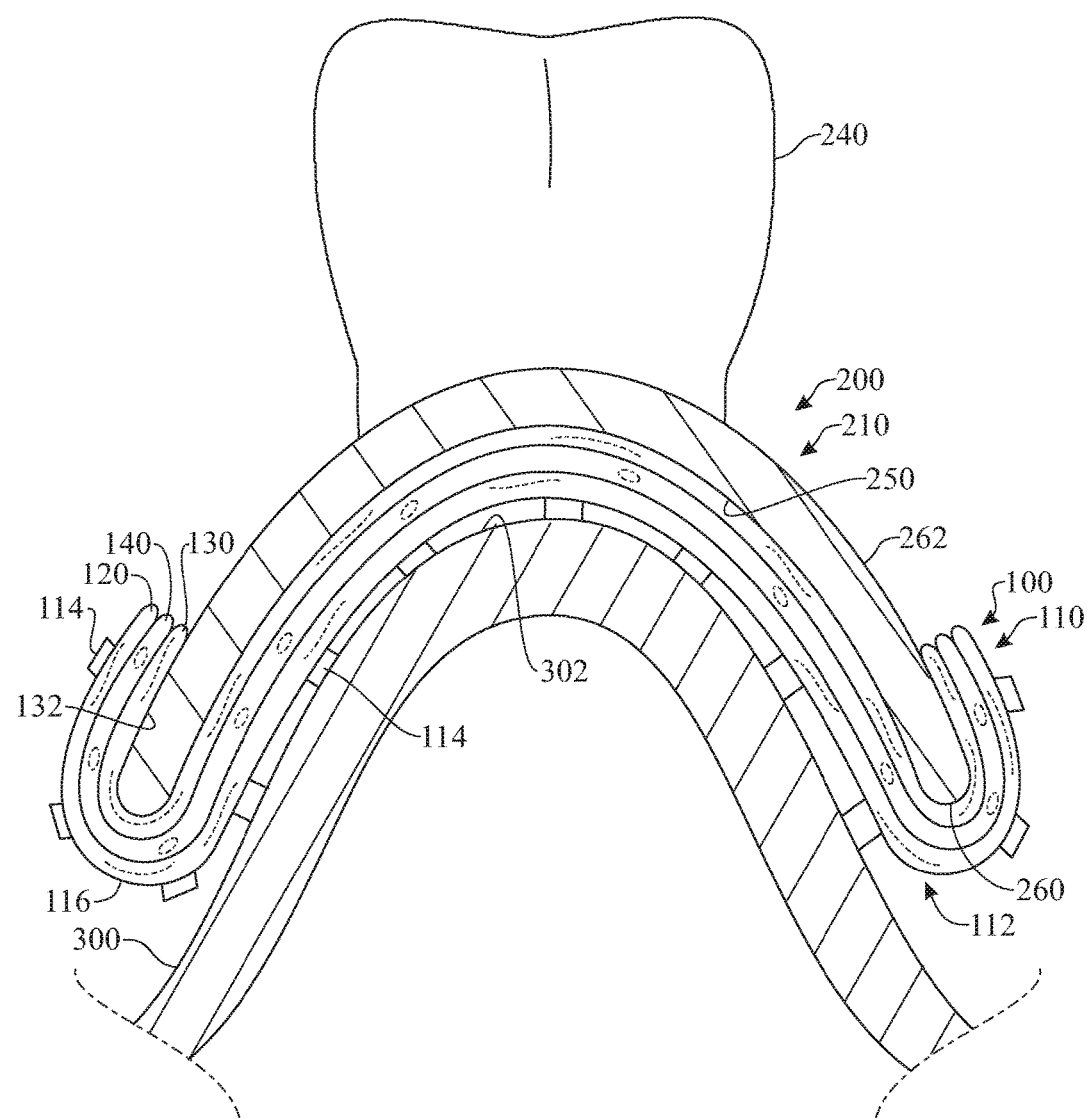
FIG. 20 presents a cross-sectional, front elevation view of the assembly of FIG. 19, the cross section taken along the first side or the second side of the denture.

The illustrations of FIGS. 13-20 show a denture-securing device 100 for securing a denture to a human gum in accordance with a further embodiment of the present disclosure. The denture-securing device 100 comprises a flexible and absorbent main body or pad 110 installable on a denture that is affixable to a human gum, such as a lower denture 200 as shown in FIG. 16 or an upper denture (not shown, but otherwise similar to upper denture 16 or to an inverted version of lower denture 200). As further shown in FIG. 16, the denture 200 is provided with a first side 210, an opposite second side 220 and a front side 230 extending from and connecting the first side 210 to the second side 220. The denture comprises a plurality of artificial teeth 240 arranged in opposition to a denture channel 250, as best shown in FIG. 20. As will be described in detail hereinafter, the absorbent and flexible pad 110 constitutes a single pad which is installable on and configured to cover the first side 210, second side 220 and front side 230 of the denture 200.

In some embodiments of the invention, the pad 110 can be constructed from wood pulp paper. Alternatively or additionally, the pad 100 can be constructed from fabric, cotton, pure cellulose, linen fibers, lignin, spun lace cotton, or a combination thereof.

As best shown in FIG. 14, the pad 110 comprises an embossed outer side 112 configured to face a human gum when the pad 110 is installed on the denture 200. By embossed, it is understood that said outer surface 112 includes raised portions, reliefs or protrusions 114 which are raised against a background or floor 116 of the embossed outer side 112. As will be described hereinafter, the embossing provides an enhanced adherence between the pad 110 and the denture user's gum, and thus an improved attachment of the denture 200 to the gum.

Figure 13:
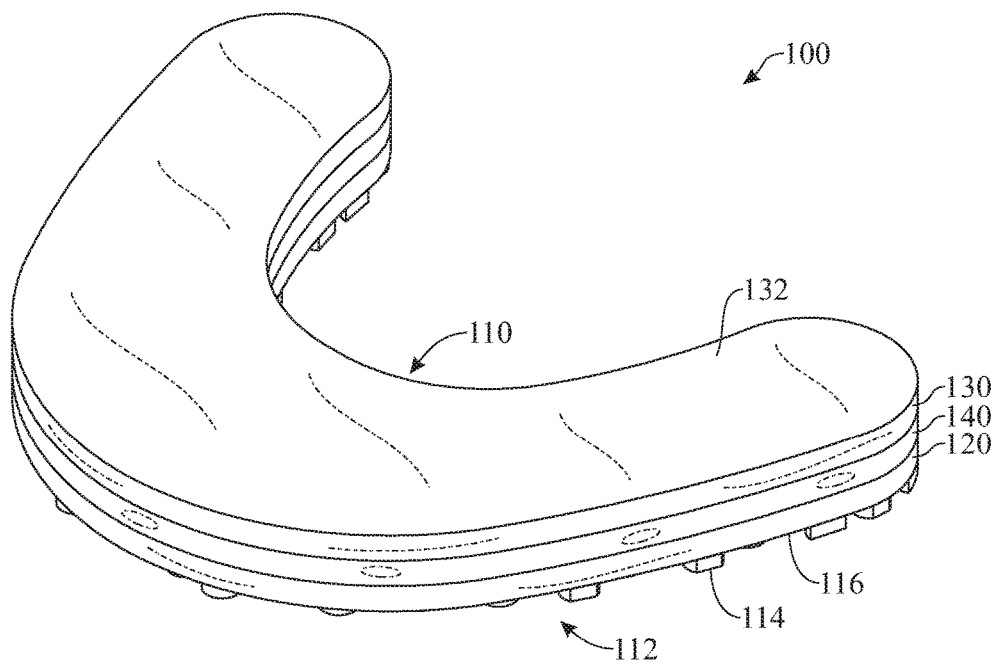
FIG. 13 presents a top perspective view of a denture-securing device in accordance with another embodiment of the invention, wherein the denture-securing device includes an embossed outer surface.

As further shown in FIGS. 13-15, the pad 110 can include multiple layers of material, which allows different sections of the pad 110 to be manufactured using a different material for specific purposes. In some embodiments of the invention, the multiple layers of material can include at least two separate pieces of the material arranged in layers. For instance and without limitation, the at least two, multiple layers of material of the pad 110 can include an outer layer 120 providing the embossed outer side 112, an inner layer 130 providing an inner surface 132 configured to contact and adhere to the denture 200, and an intermediate layer 140 sandwiched between the outer layer 120 and the inner layer 130. In some embodiments, the outer layer 120 can be constructed of pure cellulose. Alternatively or additionally, the inner layer 130 can be constructed of spun lace cotton. Alternatively or additionally, the intermediate layer 140 can be constructed of cotton. In some embodiments, the edges of the multiple layers of material (e.g. the outer, inner and intermediate layers 120, 130 and 140) can be stitched to one another.

Alternative embodiments are contemplated, however, in which the multiple layers of material can include a single piece of material folded so as to be configured into at least two layers. Further alternative embodiments are contemplated in which combinations of separate pieces arranged in layers with a folded material providing at least two layers can be included in the pad. In general, similarly to the previous embodiments, the material(s) used for constructing the pad 110 may be folded and/or stacked in order to provide the denture-securing device with the desired thickness.

Figure 17:
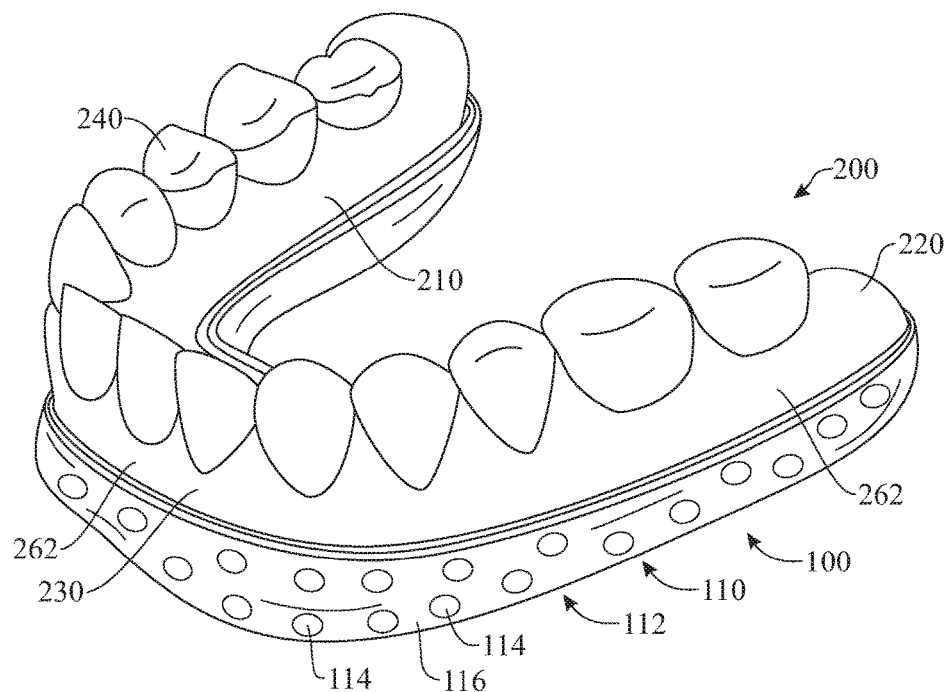
FIG. 17 presents a perspective view illustrating a second step of installing the denture-securing device, and more specifically showing the denture-securing device installed on the denture.
Figure 18:
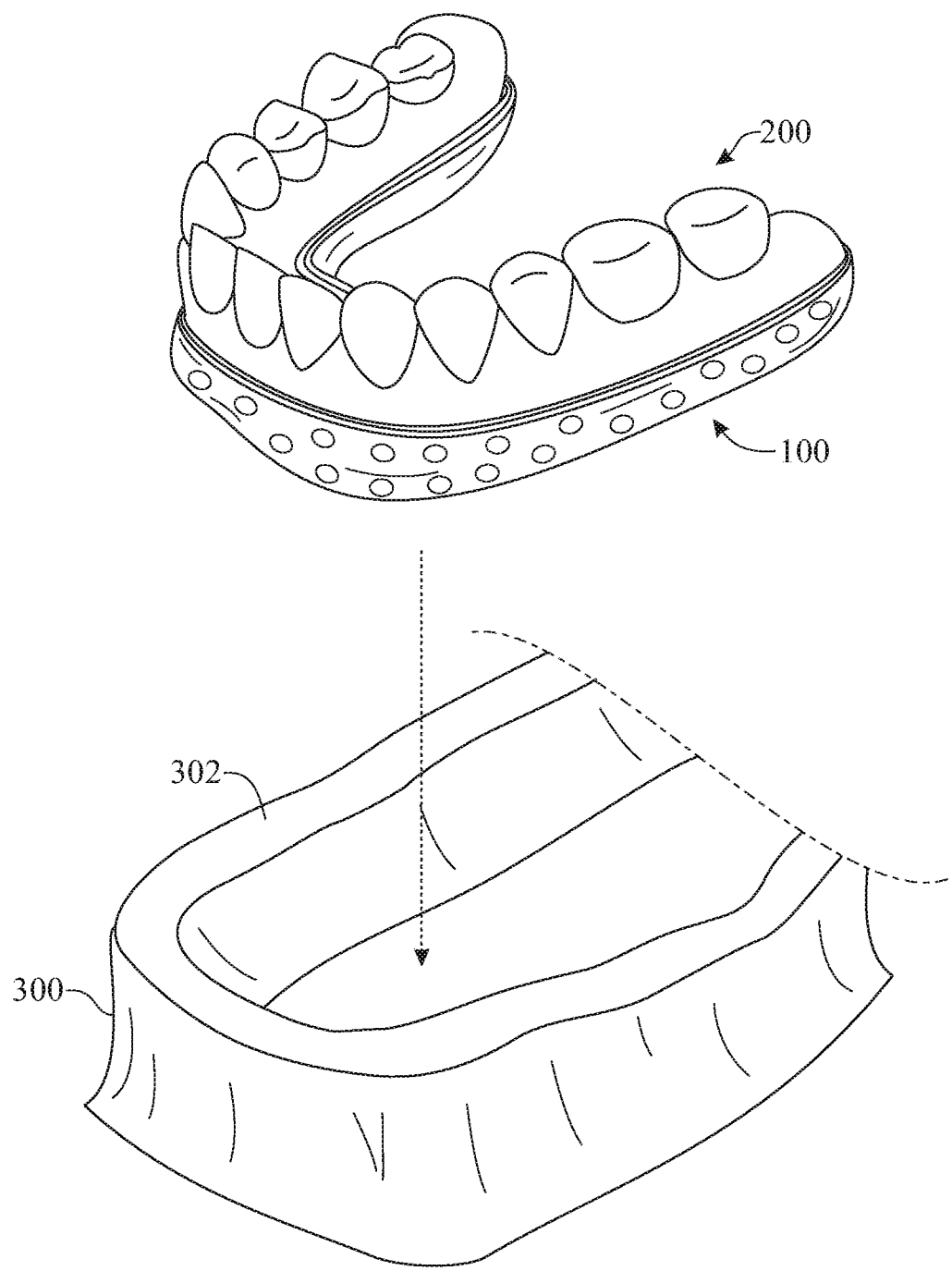
FIG. 18 presents a perspective view illustrating a third step of installing the denture-securing device, and more specifically illustrating placement of the denture-securing device and denture on a user's gum.
Figure 19:
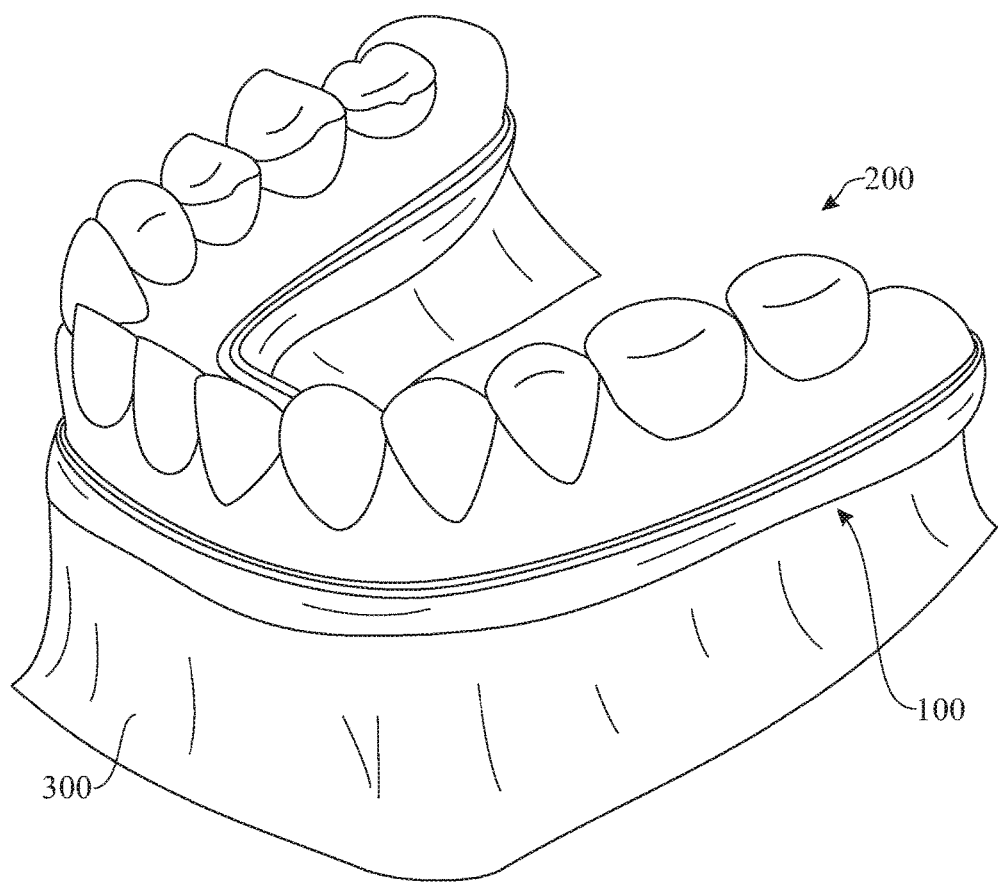
FIG. 19 presents a perspective view illustrating a third step of installing the denture-securing device, and more specifically showing the denture-securing device and denture installed on the gum.

The illustrations of FIGS. 16-20 show a sequence of steps for installing the denture-securing device 100 and a denture 200 on a gum 300 of a denture user. As shown in FIG. 16, the denture-securing device 100 is installed in a denture channel 250 (better shown in FIG. 20) such that the inner surface 132 of the pad 110 rests against the denture 200 and the opposite, embossed outer surface 112 of the pad 110 faces outwardly of the denture 200. As shown in FIG. 17, the flexible pad 110 is wrapped around or folded over an outer edge 260 of the denture 200, and overlaps and is in contact with an outer face 262 of the denture 200. Next, as shown in FIG. 18, the denture 200 and denture-securing device 100 can be placed on a denture user's gum 300 such that an outer edge 302 of the gum 300 is received within the denture channel 250, with the pad 110 sandwiched between the gum 300 and the denture 200, as shown in the perspective view of FIG. 19 and the cross-sectional view of FIG. 20. In this working position shown in FIGS. 19 and 20, the pad 110 is moistened by saliva and/or another applicable liquid (for instance, by applying water to the pad 110 prior to installing the pad 110 on the denture 200) and, by pressing the moistened pad 110 against the gum 300, the pad 110 compresses and expels part of the absorbed liquid, and then tends to expand, causing the pad 110 to become adhered to the gum 300 via suction of the gum 300 towards the embossed pad 110. This suctioning effect of the gum 300 towards the pad 110 is enhanced by the fact that the outer side 112 of the pad 110 is embossed. The pad 110 also remains attached to the denture 200 by a suctioning of the denture 200 towards the inner surface 132 of the pad 110. Though not specifically shown, in some embodiments of the invention the inner surface 132 may also be embossed to enhance the suctioning effect. Thus, the pad 110 attaches the denture 200 to the gum 300 without the use of adhesives. Furthermore, by folding over the edge 260 and onto the outer face 262 of the denture 260, the pad 110 decreases rocking of the denture 200, contributes to the suction, and helps prevent food from getting between the denture 200 and the gum 300, which can cause pain when chewing.

The denture-securing device 100 is cleanable and reusable. For instance, after the user has finished eating, the pad 110 can be rinsed and reapplied to the denture 200 and gum 300.

The denture-securing device may advantageously secure dentures without requiring use of adhesives. The denture-securing device may also reduce the likelihood of food getting under dentures, provide a firm yet soft fit, and minimize rocking of lower dentures and partials. The denture-securing device may advantageously be secured to gums using a suction fit.

Alternative embodiments are contemplated in which the denture-securing device 200 may be divided into two pads, similarly to the embodiment of FIGS. 1-5. I.e., the denture-securing device 200 may comprise a first pad installable on the first side 210 of the denture 200 and a separate, second pad installable on the opposite second side 220 of the denture 200.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A denture and denture-securing device assembly comprising:
   a denture that is affixable to a human gum of a human mouth, the denture comprising a first side and a second side affixable to the gum at left and right sides of the mouth, respectively, the denture further comprising a channel configured to receive the gum, wherein an outer face of the denture is configured to be arranged outward of the gum when the gum is received within the channel, the outer face of the denture terminating in an outer edge; and
   a denture-securing device for securing the denture to the gum, the denture-securing device comprising at least one absorbent and flexible pad installable on the first side and the opposite second side of the denture, wherein the at least one pad comprises an embossed outer side configured to face a human gum when the pad is installed on the denture; and further wherein
   the denture-securing device is mounted on the denture such that the at least one pad is flexed and placed into the channel of the denture, and a portion of the at least one pad folds over the outer edge of the denture and covers the outer face of the denture at least partially, and such that the at least one pad is configured to be sandwiched between the denture and a human gum and to be moistened and adhered to the human gum via suction of the human gum towards the embossed outer side of the at least one pad.

2. The denture and denture-securing device assembly of claim 1, wherein the at least one pad comprises a first pad installable on the first side of the denture and a second pad installable on the opposite second side of the denture.

3. The denture and denture-securing device assembly of claim 1, wherein the at least one pad comprises a single pad installable on the first side, the opposite second side and a front side of the denture extending from the first side to the second side of the denture.

4. The denture and denture-securing device assembly of claim 1, wherein the at least one pad is comprised of multiple layers of material.

5. The denture and denture-securing device assembly of claim 4, wherein the multiple layers of material comprise an outer layer providing the embossed outer side, an inner layer providing an inner surface configured to contact the denture, and an intermediate layer sandwiched between the outer layer and the inner layer.

6. The denture and denture-securing device assembly of claim 5, wherein the outer layer is made of pure cellulose.

7. The denture and denture-securing device assembly of claim 5, wherein the inner layer is made of spun lace cotton.

8. The denture and denture-securing device assembly of claim 5, wherein the intermediate layer is made of cotton.

9. The denture and denture-securing device assembly of claim 4, wherein the multiple layers of material comprise at least two separate pieces of the material arranged in layers.

10. The denture and denture-securing device assembly of claim 4, wherein the multiple layers of material comprise a single piece of material folded so as to be configured into at least two layers.

11. The denture and denture-securing device assembly of claim 4, wherein the multiple layers of material comprise at least two separate pieces of material, wherein each separate piece of material is folded so as to be configured into at least two layers, and wherein the at least two separate pieces of material are arranged in layers after folding.

12. The denture and denture-securing device assembly of claim 1, wherein the pad is constructed from wood pulp paper.

13. The denture and denture-securing device assembly of claim 1, wherein the pad is constructed from fabric, cotton, pure cellulose, linen fibers, lignin, spun lace cotton, or a combination thereof.

14. The denture and denture-securing device assembly of claim 1, wherein the pad is cleanable and reusable.

15. The denture and denture-securing device assembly of claim 1, wherein the denture is an upper denture or a lower denture.

16. The denture and denture-securing device assembly of claim 1, the at least one pad is moistened by saliva or water present in a user's mouth.

17. A denture and denture-securing device assembly comprising:
   a denture that is affixable to a human gum of a human mouth, the denture comprising a first side and a second side affixable to the gum at left and right sides of the mouth, respectively, the denture further comprising a channel configured to receive the gum, wherein an outer face of the denture is configured to be arranged outward of the gum when the gum is received within the channel, the outer face of the denture terminating in an outer edge; and
   a denture-securing device for securing the denture to the gum, the denture-securing device comprising at least one absorbent and flexible pad installable on the first side and the opposite second side of the denture, wherein the at least one pad comprises an outer layer, an inner layer and an intermediate layer arranged between the outer and inner layers, wherein the outer layer comprises an embossed outer side configured to face a human gum when the pad is installed on the denture, and the inner layer comprises an inner surface arranged opposite to the embossed outer side of the outer layer; and further wherein the denture-securing device is mounted on the denture such that the at least one pad is flexed and placed into the channel of the denture, and a portion of the at least one pad folds over the outer edge of the denture and covers the outer face of the denture at least partially, and such that the at least one pad is configured to be sandwiched between the denture and a human gum, to be moistened and adhered to the human gum via suction of the human gum towards the embossed outer side of the at least one pad, and to be adhered to the denture via suction of the denture towards the inner surface of the pad.

* * * * *